(12) United States Patent
Tsai et al.

(10) Patent No.: US 9,730,772 B2
(45) Date of Patent: Aug. 15, 2017

(54) BONE IMPLANT DRILL

(71) Applicant: METAL INDUSTRIES RESEARCH & DEVELOPMENT CENTRE, Kaohsiung (TW)

(72) Inventors: Tung-Lin Tsai, Kaohsiung (TW); E-Hsung Cheng; Bo-Wei Pan, Kaohsiung (TW); Pei-Hua Wang, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 395 days.

(21) Appl. No.: 14/606,106

(22) Filed: Jan. 27, 2015

(65) Prior Publication Data

US 2016/0081775 A1 Mar. 24, 2016

(30) Foreign Application Priority Data

Sep. 18, 2014 (TW) .............................. 103132264 A

(51) Int. Cl.
*A61B 17/16* (2006.01)
*A61C 8/00* (2006.01)
*A61C 1/18* (2006.01)

(52) U.S. Cl.
CPC ........ *A61C 8/0092* (2013.01); *A61B 17/1695* (2013.01); *A61C 1/18* (2013.01)

(58) Field of Classification Search
CPC .... A61C 8/0092; A61B 17/16; A61B 17/1695
See application file for complete search history.

(56) References Cited

U.S. PATENT DOCUMENTS

| | | | | |
|---|---|---|---|---|
| 1,699,870 A | * | 1/1929 | Black | B23B 45/008 173/13 |
| 3,515,100 A | * | 6/1970 | Keller | A61B 17/1695 408/14 |
| 4,456,010 A | * | 6/1984 | Reimels | A61B 17/1695 408/139 |
| 8,029,523 B2 | * | 10/2011 | Wallis | A61B 17/1688 408/132 |

(Continued)

FOREIGN PATENT DOCUMENTS

WO WO2014062025 A1 4/2014

*Primary Examiner* — Nicholas Woodall
(74) *Attorney, Agent, or Firm* — Alan D. Kamrath; Kamrath IP Lawfirm, P.A.

(57) ABSTRACT

A bone implant drill includes a bearing received in a sleeve. A transmission shaft includes a rod extending through the bearing and a transmission member formed on an end of the rod and received in the sleeve. The other end of the rod extends beyond the sleeve. A cutting rod includes a cutter, a coupling member received in the sleeve, and a positioning member between the cutter and the coupling member. The cutter and the coupling member are provided on two ends of the cutting rod respectively. The coupling member includes second teeth releasably engageable with first teeth on a free end of the transmission member. An elastic element is mounted in the sleeve. The elastic element includes a first end mounted around the coupling member and abutting the positioning member. The elastic element further includes a second end mounted around the transmission member and abutting the bearing.

10 Claims, 6 Drawing Sheets

(56) References Cited

U.S. PATENT DOCUMENTS

| | | | |
|---|---|---|---|
| 2008/0243123 A1* | 10/2008 | Gordils Wallis ... | A61B 17/1688 |
| | | | 606/80 |
| 2010/0121330 A1* | 5/2010 | Parmigiani ........ | A61B 17/1617 |
| | | | 606/79 |
| 2011/0008746 A1 | 1/2011 | Kim | |
| 2013/0171585 A1 | 7/2013 | Huang et al. | |

* cited by examiner

BONE IMPLANT DRILL

BACKGROUND OF THE INVENTION

1. Field of the Invention

The present invention relates to a drill and, more particularly, to a bone implant drill that is suitable for a bone implant and that can be coupled with a drilling machine to proceed with a drilling operation for bone implantation.

2. Description of the Related Art

During a dental implant surgery, the surgeon generally drills a hole in the alveolar bone of a patient before tightly implanting an implant into the alveolar bone. In a dental implant surgery of an upper jaw, in a case that the height of the bone ridge of the upper jaw of the patient is insufficient, it is necessary to lift the sinus membrane of the patient and to graft bone before implanting the implant, avoiding the implant from penetrating the sinus membrane. Such a surgery is referred to as a sinus lifting operation.

The sinus lifting operation includes two commonly used methods: a window method and a bone chisel method. The operation is decided by the residual height of the alveolar bone. Namely, the window method requiring a longer treatment time is adopted if the residual height of the alveolar bone is smaller than 5 mm. The bone chisel method can be used if the residual height of the alveolar bone is equal to or larger than 5 mm.

Specifically, the bone chisel method includes using a hammer to strike a bone chisel, causing perforating fracture at the bottom of the paranasal sinus by hammering. An edge of a recessed portion in a top end of the bone chisel is used to scrape the ambient bone into the paranasal sinus. The bone scraps protect the sinus membrane from tear and perforation during lifting of the paranasal sinus. Furthermore, the autogenous bone is helpful in generation of a new bone without the need of obtaining a bone, reducing the loss of the autogenous bone. The costs are reduced, because artificial bone implantation is not required.

To avoid the sinus membrane of the patient from being broken by the bone chisel, the surgeon generally proceeds a preoperative planning by computerized tomography to check the height and density of the bone. However, operation of the bone chisel method largely relies on the experience and the hand feel of the surgeon, and it is not uncommon that the patient suffers from clinical aftereffects including dizziness or even concussion due to an excessive hammering force.

FIG. 1 shows a conventional bone implant drill 9 including a column 91, a transmission shaft 92, an elastic element 93, and a sealing member 94. A cutter 911 is provided on an end of the column 91. A coupling seat 912 is provided on the other end of the column 91. A transmission seat 921 is provided on an end of the transmission shaft 92 for meshing with a toothed portion of the coupling seat 912. The other end of the transmission shaft 92 can be coupled to an electric hand piece H for driving the transmission shaft 92 to rotate. Two ends of the elastic element 93 are respectively connected to the coupling seat 912 and the transmission seat 921. The sealing member 94 envelops the coupling seat 912, the elastic element 93, and the transmission seat 921.

When the cutter 911 encounters a resistance, the transmission seat 921 compresses the elastic element 93 and engage with the coupling seat 921, causing synchronous rotation of the column 91. The resistance exerting on the cutter vanishes at the moment the cutter 911 penetrates the cortical bone, and the elastic element 93 immediately disengages the transmission seat 921 from the coupling seat 912 such that the transmission shaft 92 no longer rotates jointly with the column 91, effectively avoiding the cutter 911 from keeping cutting and, hence, injuring the nasal membrane of the patient. An example of such a bone implant drill is disclosed in US Patent Publication No. 2013/0171585 entitled "APPARATUS FOR LIFTING MAXILLARY SINUS".

However, the two ends of the elastic element 93 of the conventional bone implant drill 9 directly abut an interior of the coupling seat 912 and an interior of the transmission seat 921, such that the moment the elastic element 93 disengages the transmission seat 921 from the coupling seat 912, a speed difference is generated between the column 91 that stops rotating and the elastic element 93 that still rotates jointly with the transmission shaft 92 at a high speed (normally higher than 2000 rpm). Thus, heat is generated due to the friction between an end of the elastic element 93 and the coupling seat 912. As a result, the column 91 directly contacting the bone cells is apt to be in a high temperature state. Ostenonecrosis resulting from bone necrosis fever is apt to occur if the contact temperature exceeds 60☐. Although water spray can be provided to reduce the temperature of the outer portion of the column 91 to be below 60☐, the cutter 911 of the column 91 still has the risk of excessively high temperature.

Furthermore, the high temperature resulting from friction also adversely affects the function of the elastic element 93. Thus, the elastic element 93 whose elasticity has been compromised in the previous high-temperature operation cannot reliably disengage the transmission seat 921 from the coupling seat 912 at the moment the cutter 911 of the column 91 penetrates the cortical bone, such that the column 91 keeps rotating and injures the nasal membrane of the patient by the cutter 911. Thus, the conventional bone implant drill 9 cannot operate continuously and, thus, provides poor use convenience.

Furthermore, the elastic element 93 is not supported from the inside and is, thus, liable to twist and deform, failing to disengage the transmission seat 921 from the coupling seat 912. The twisted and deformed elastic element 93 could even hook the toothed portion of the transmission seat 921 such that the column 91 cannot stop rotating at the moment the cutter 91 penetrates the cortical bone, which also results in injury to the nasal membrane of the patient.

Furthermore, the speed difference between the column 91 and the elastic element 93 tends to wear the coupling seat 912 or damage the elastic element 93 after a long period of time of use. The service life of the conventional bone implant drill 9 is, thus, adversely affected.

Thus, improvement to the conventional bone implant drills is required.

SUMMARY OF THE INVENTION

An objective of the present invention is to provide a bone implant drill including an elastic element that will not cause wear to nor will not be worn by the components that are still rotating or that have stopped rotating.

Another objective of the present invention is to provide a bone implant drill including an elastic element whose elasticity can well be maintained, reliably achieving the effect of the safety mechanism of the bone implant drill while permitting continuous operation.

A further objective of the present invention is to provide a bone implant drill including an elastic element that is less likely to twist and deform.

The present invention fulfills the above objectives by providing a bone implant drill including a sleeve and a bearing received in the sleeve. A transmission shaft includes a rod and a transmission member. The rod extends through the bearing. The transmission member is formed on an end of the rod and is received in the sleeve. The transmission member includes a free end with a plurality of first teeth. The other end of the rod extends beyond the sleeve. A cutting rod includes a cutter, a positioning member, and a coupling member. The cutter and the coupling member are provided on two ends of the cutting rod respectively. The positioning member is located between the cutter and the coupling member. The coupling member is received in the sleeve. The coupling member includes a plurality of second teeth releasably engageable with the plurality of first teeth. An elastic element is mounted in the sleeve. The elastic element includes a first end mounted around the coupling member and abutting the positioning member. The elastic element further includes a second end mounted around the transmission member and abutting the bearing.

The bearing can include an inner race and an outer race surrounding the inner race. The outer race and the inner race are rotatable relative to each other. The rod extends through and is coupled to the inner race. The rod and the inner race are jointly rotatable. The second end of the elastic element abuts the outer race.

The transmission member can have a diameter larger than a diameter of the rod, forming a shoulder at an interconnection between the transmission member and the rod. The shoulder abuts the inner race of the bearing and does not abut the outer race of the bearing.

The bone implant drill can further include a limiting ring. The rod of the transmission shaft extends through and is coupled to the limiting ring. The rod and the limiting ring are jointly rotatable. The bearing is restricted between the limiting ring and the transmission member. The limiting ring abuts the inner race of the bearing and does not abut the outer race of the bearing.

The sleeve can include an open first end through which the rod extends. The sleeve can further include an inner flange in the first end thereof. The outer race of the bearing abuts the inner flange. The inner race of the bearing does not abut the inner flange.

The sleeve can further include an open second end. The positioning member of the cutting rod can be connected to the coupling member. The positioning member has a diameter larger than a diameter of the coupling member, forming a shoulder at an interconnection between the positioning member and the coupling member. The cutting rod is coupled to the second end of the sleeve by the positioning member. The first end of the elastic element abuts the shoulder.

The plurality of second teeth can mesh with the plurality of first teeth by rectilinear contact.

The cutting rod and the rod can be coaxial to each other. The plurality of first teeth surrounds and is centered on an axis of the rod. The plurality of second teeth surrounds and is centered on an axis of the cutting rod. Each of the plurality of first and second teeth includes decreasing widths from a root thereof towards a free end thereof and includes an outer face and an inner face opposite to the outer face. The free end of each of the plurality of first and second teeth extends arcuately from the outer face to the inner face.

Each of the plurality of first and second teeth cam further include two lateral faces connected between the outer face and the inner face. Each of the two lateral faces inclines from the outer face towards the inner face such that the inner face is smaller than the outer face.

The bone implant drill can further include another bearing. The two bearings can be coaxial to each other. The transmission shaft extends through the two bearings.

The elastic element 5 of the bone implant drill will not cause wear to nor will not be worn by the components that are still rotating or that have stopped rotating, prolonging the service life of the components, avoiding annoying noise during operation, and preventing temperature increase of the components contacting the object being drilled. Thus, when the bone implant drill is used to drill a bone of a creature, the risks of osteonecrosis can be reduced. Furthermore, the elastic element is not only less likely to twist and deform but can maintain good elasticity to reliably achieve the effect of the safety mechanism of the bone implant drill while permitting continuous operation to increase the drilling efficiency.

The present invention will become clearer in light of the following detailed description of illustrative embodiments of this invention described in connection with the drawings.

BRIEF DESCRIPTION OF THE DRAWINGS

The illustrative embodiments may best be described by reference to the accompanying drawings where.

DETAILED DESCRIPTION OF THE INVENTION

Figure 2:
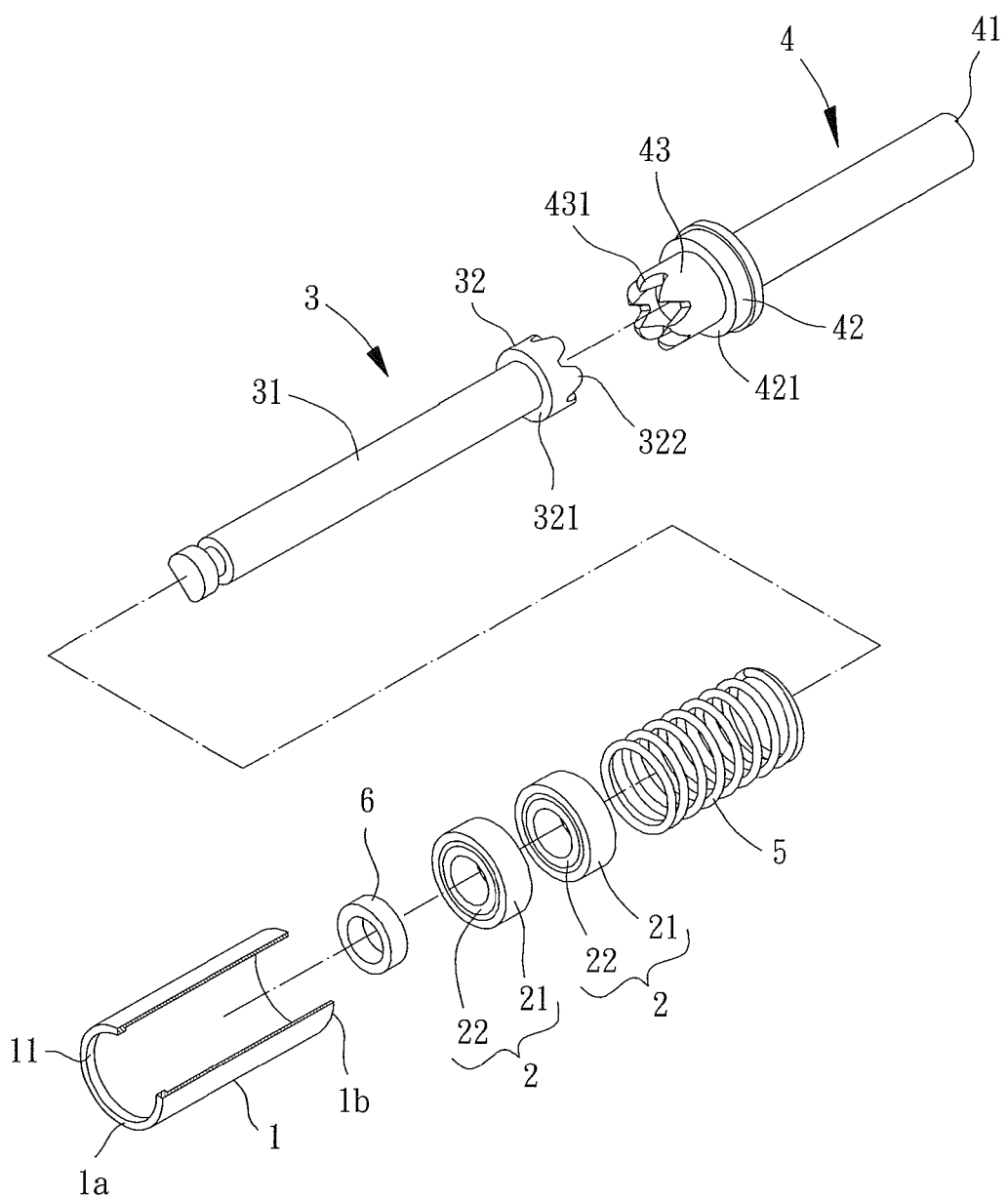
FIG. 2 is an exploded, perspective view of a bone implant drill of an embodiment according to the present invention.
Figure 3:
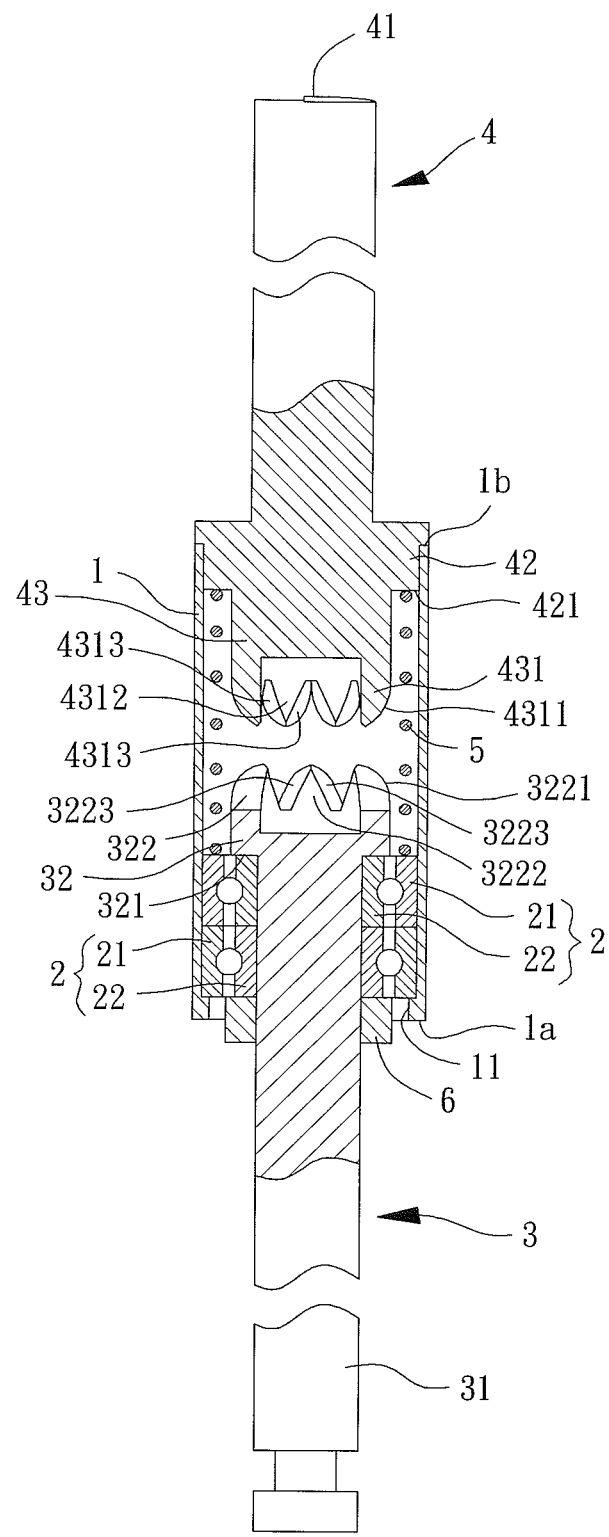
FIG. 3 is a cross sectional view of the bone implant drill of FIG. 2.

With reference to FIGS. 2 and 3, a bone implant drill of an embodiment according to the present invention includes a sleeve 1, a bearing 2 received in the sleeve 1, a transmission shaft 3, a cutting rod 4, and an elastic element 5. The transmission shaft 3 extends through the bearing 2. An end of the transmission shaft 3 can mesh with an end of the cutting rod 4 or disengage from the end of the cutting rod 4 under the action of the elastic element 5. The other end of the transmission shaft 3 and the other end of the cutting rod 4 extend beyond the sleeve 1.

The sleeve 1 includes a first end 1a and a second end 1b. The first and second ends 1a and 1b of the sleeve 1 are open. The sleeve 1 further includes an inner flange 11 in the first end 1a. The bearing 2 abuts the inner flange 11 to avoid the bearing 2 from falling from the first end 1a of the sleeve 1.

The bearing 2 received in the sleeve 1 can be of any type, such as an oily bearing or a bearing including inner and outer races rotatable to each other, such as a ball bearing, a roller bearing, or a cone bearing. In this embodiment, the bearing 2 is, but not limited to, a ball bearing. Specifically, the bearing 2 includes an inner race 22 and an outer race 21 surrounding the inner race 22. The inner race 22 and the outer race 21 can rotate relative to each other. The bone implant drill can further include another bearing 2. The two bearings 2 are coaxial to each other, and the transmission shaft 3 extends through the two bearings 2 to prevent swaying of an axis of the transmission shaft 3, increasing the rotational stability of the transmission shaft 3. An outer one of the two bearings 2 is adjacent to the inner flange 11. The outer race 21 of the outer one of the two bearings 2 abuts the inner flange 11, but the inner race 22 of the outer one of the two bearings 2 does not abut the inner flange 11.

The transmission shaft 3 includes a rod 31 and a transmission member 32. The rod 31 extends through and is coupled to the two bearings 2 such that the transmission shaft 3 and the two bearings 2 can rotate jointly. The transmission member 32 is formed on an end of the rod 31 and is received in the sleeve 1. The transmission member 32 has a diameter larger than a diameter of the rod 31, forming a shoulder 321 at an interconnection between the transmission member 32 and the rod 31. The shoulder 321 abuts the inner race 22 of the bearing 2 but does not abut the outer race 21 of the bearing 2. The other end of the rod 31 extends beyond the sleeve 1.

The transmission member 32 includes a free end with a plurality of first teeth 322. In this embodiment, the first teeth 322 surround and are centered on an axis of the rod 31. Each first tooth 322 is substantially an isosceles triangle in cross section. Each first tooth 322 includes decreasing widths from a root thereof towards a free end thereof. Each first tooth 322 further includes an outer face 3221, an inner face 3222 opposite to the outer face 3221, and two lateral faces 3223 connected between the outer face 3221 and the inner face 3222. Each first tooth 322 can be rounded at the free end thereof, such that the free end of each first tooth 322 extends arcuately from the outer face 3221 to the inner face 3222. Each lateral face 3223 inclines from the outer face 3221 towards the inner face 3222 such that the inner face 3222 is smaller than the outer face 3221.

The cutting rod 4 includes a cutter 41, a positioning member 42, and a coupling member 43. The cutter 41 and the coupling member 43 are provided on two ends of the cutting rod 4 respectively. The positioning member 42 is located between the cutter 41 and the coupling member 43 and is close to the coupling member 43. In this embodiment, the positioning member 42 of the cutting rod 4 is connected to the coupling member 43. Furthermore, the positioning member 42 has a diameter larger than a diameter of the coupling member 43, forming a shoulder 421 at an interconnection between the positioning member 42 and the coupling member 43.

The cutting rod 4 is coupled to the second end 1b of the sleeve 1 by the positioning member 42. The coupling member 43 is received in the sleeve 1. The coupling member 43 includes a plurality of second teeth 431 releasably engageable with the first teeth 322. In this embodiment, the cutting rod 4 and the rod 31 are coaxial to each other. The second teeth 431 surround and are centered on an axis of the cutting rod 4. Each second tooth 431 is a substantially an isosceles triangle in cross section.

Each second tooth 431 includes increasing widths from a root thereof towards a free end thereof. Each second tooth 431 further includes an outer face 4311, an inner face 4312 opposite to the outer face 4311, and two lateral faces 4313 connected between the outer face 4311 and the inner face 4312. The free end of each second tooth 431 can be rounded such that the free end of each second tooth 431 extends arcuately from the outer face 4311 to the inner face 4312. Each lateral face 4313 inclines from the outer face 4311 towards the inner face 4312 such that the inner face 4312 is smaller than the outer face 4311.

When the second teeth 431 mesh with the first teeth 322, the second teeth 431 and the first teeth 322 contact each other by rectilinear contact, which is easier to separate in comparison with surface contact.

The elastic element 5 is mounted in the sleeve 1 to provide an elastic force between the transmission member 32 and the coupling member 43. Specifically, the elastic element 5 can be a compression spring. A first end of the elastic element 5 is mounted around the coupling member 43 and abuts the shoulder 421 of the positioning member 42. A second end of the elastic element 5 is mounted around the transmission member 32 and abuts the outer race 21 of the inner one of the two bearings 2.

Figure 1:
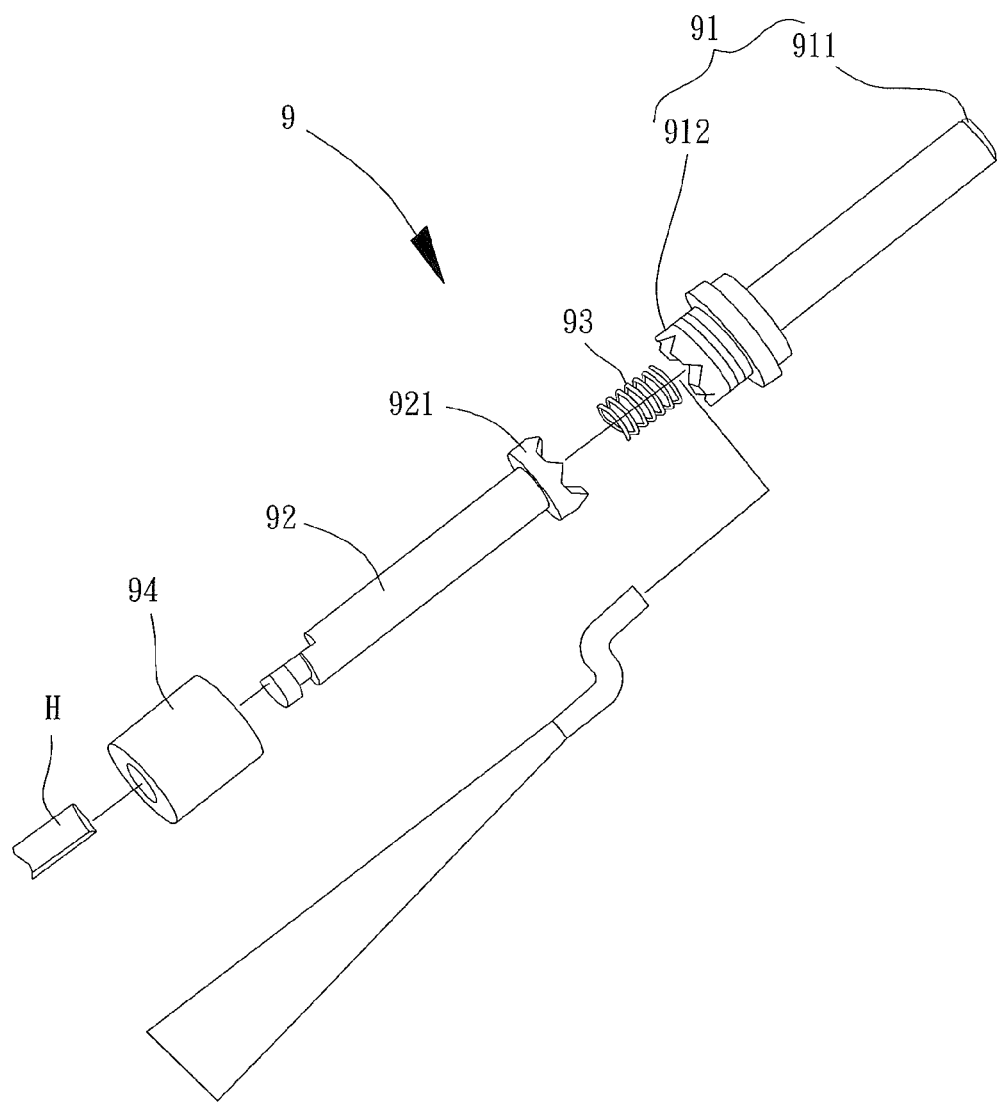
FIG. 1 is a perspective view of a conventional bone implant drill.

In comparison with the conventional bone implant drill 9 (FIG. 1) in which the elastic element 93 is mounted inside the teeth of the transmission seat 921 and the coupling seat 912, the first and second ends of the elastic element 5 are mounted around the first teeth 322 of the transmission member 32 and the second teeth 431 of the coupling member 43 and, thus, permits use of a compression spring having better elasticity. Furthermore, the first and second ends of the elastic element 5 are supported from the inside and are, thus, less likely to twist and deform.

Furthermore, the bone implant drill can further include a limiting ring 6. The rod 31 of the transmission shaft 3 extends through and is coupled to the limiting ring 6. Thus, the rod 31 and the limiting ring 6 can rotate jointly. The two bearings 2 are restricted between the limiting ring 6 and the transmission member 32. The limiting ring 6 abuts the inner race 22 of the outer one of the two bearings 2 but does not abut the outer race 21 of the outer one of the two bearings 2.

The bone implant drill according to the present invention is suitable for any drilling operation of a bone implant. The following description is a non-restrictive example of the use of the bone implant drill by coupling with an electric hand piece H (FIG. 4) for a sinus lifting operation.

Figure 4:
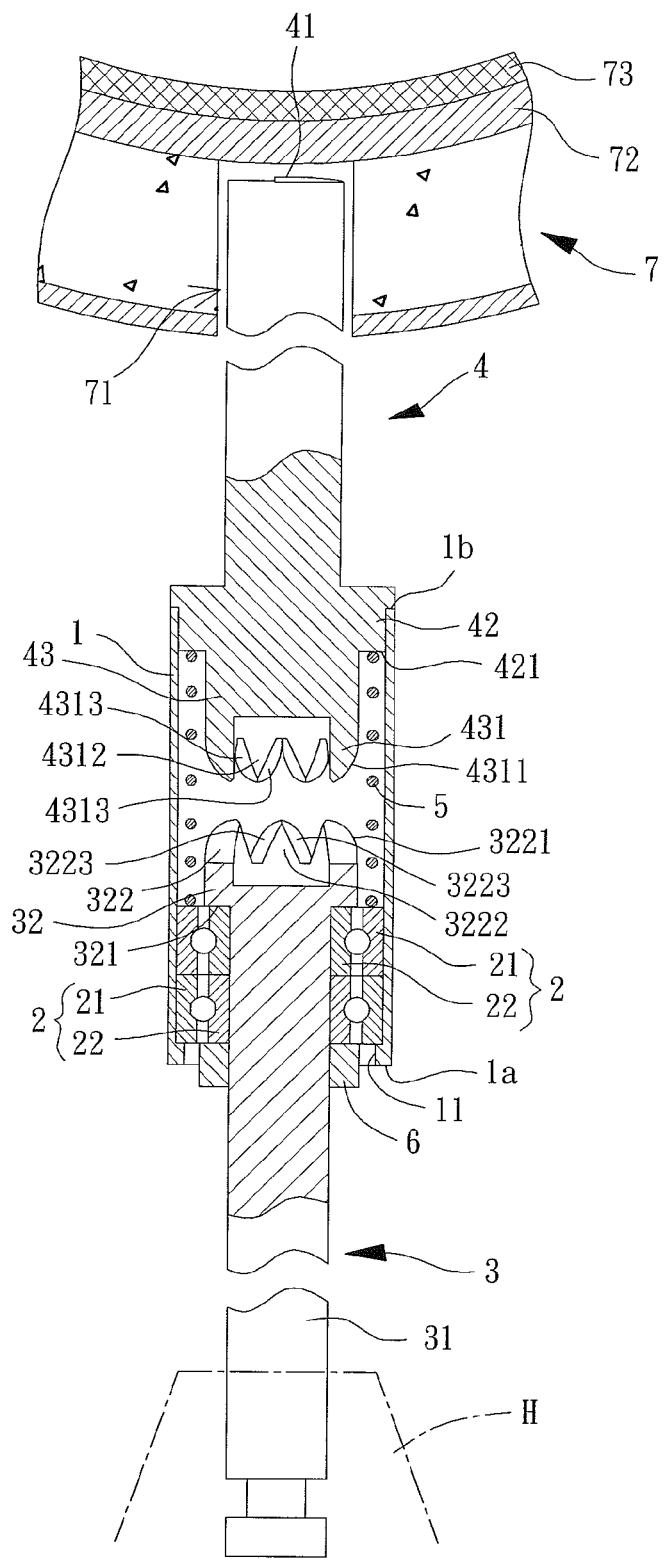
FIG. 4 is a diagrammatic cross sectional view illustrating operation of the bone implant drill of FIG. 2 with the last cortical bone not drilled.

With reference to FIG. 4, before the sinus lifting operation, a normal drilling operation is carried out to drill a hole 71 in an alveolar bone 7 of an upper jaw of a patient. The depth of the hole 71 is controlled to be spaced from the last cortical bone 72 by 1-2 mm. Then, the surgeon holds the hand piece H and aligns the cutting rod 4 with the hole 71.

Figure 5:
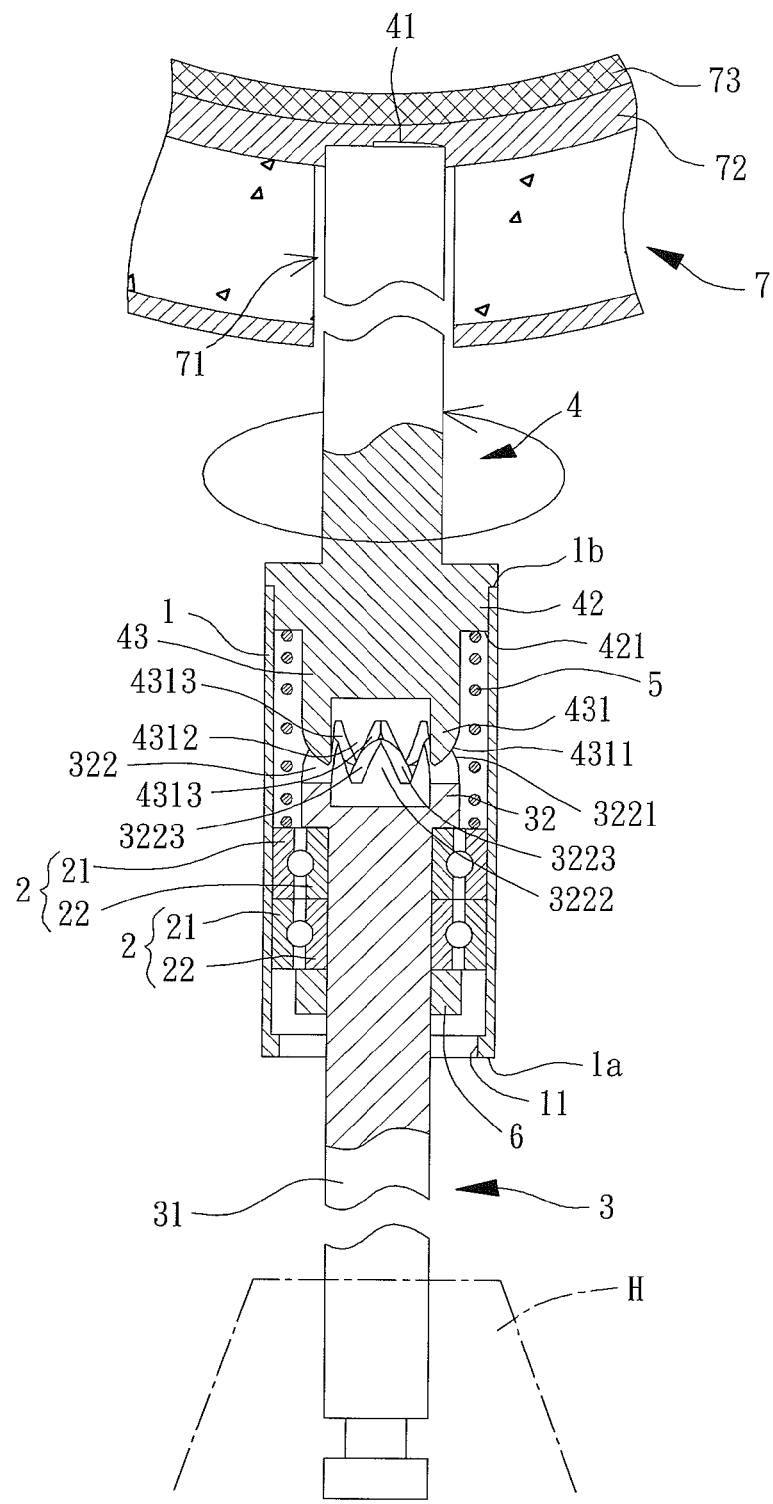
FIG. 5 is a view similar to FIG. 4 with the last cortical bone being drilled.

With reference to FIG. 5, when the surgeon applies a force on the last cortical bone 72, since the cutter 41 of the cutting rod 4 abuts a bottom end of the hole 71 and, thus, cannot be moved, the transmission shaft 3 can be moved towards the cutting rod 4 until the transmission member 32 engages with the coupling member 43. At the same time, the two bearings 2 and the limiting ring 6 move together with the rod 31 relative to the sleeve 1, such that the outer races 21 of the two bearings 2 compress the elastic element 5.

Then, the surgeon activates the hand piece H to start rotating the transmission shaft 3, which, in turn, drives the cutting rod 4 to rotate synchronously, and the cutter 41 cuts the last cortical bone 72. In this case, since all components of the bone implant drill rotate synchronously, friction resulting from speed difference of the components will not occur.

Figure 6:
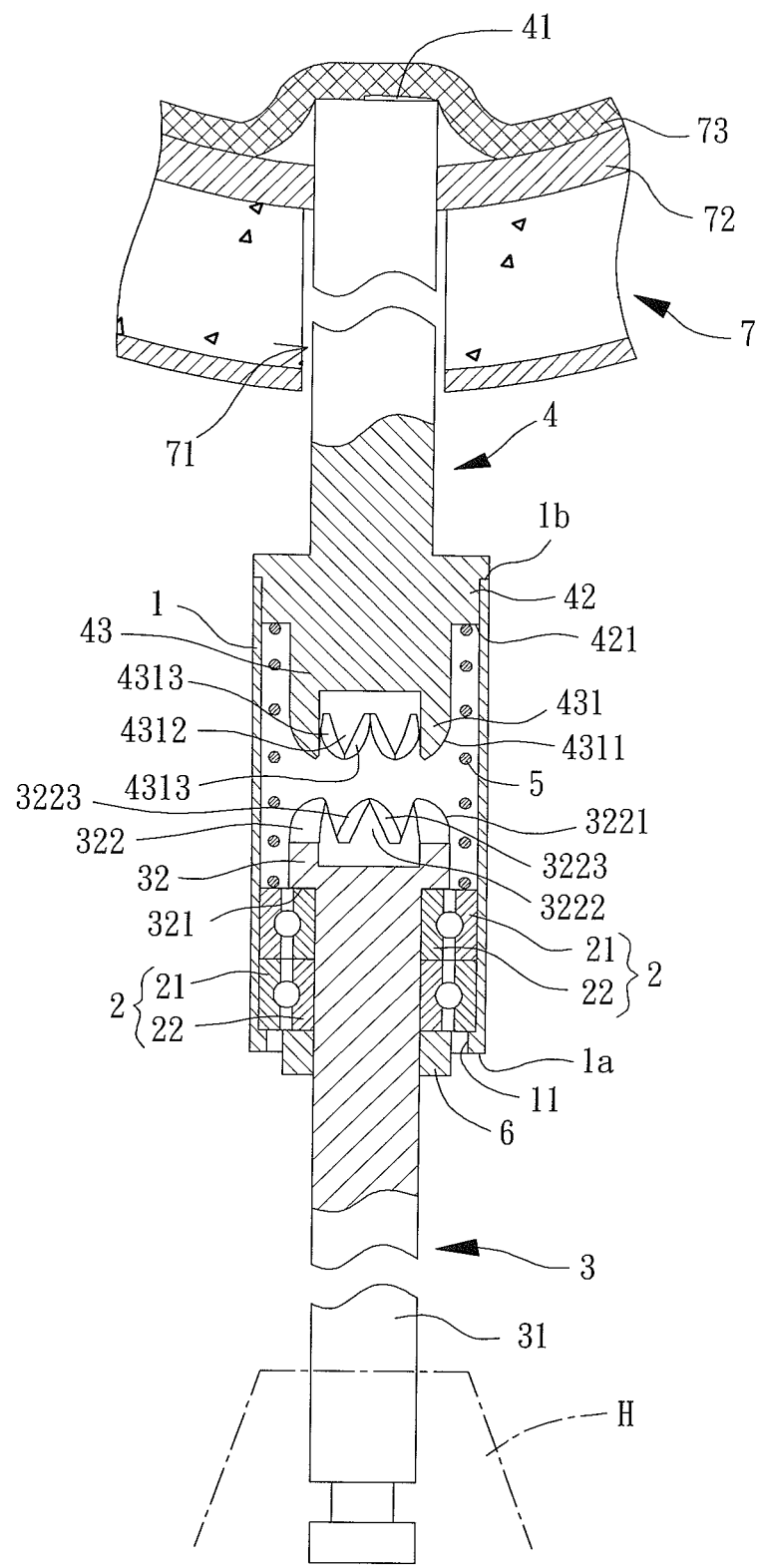
FIG. 6 is a view similar to FIG. 5 with the last cortical bone penetrated.

With reference to FIG. 6, since the resistance to the cutter 41 reduces at the moment the last cortical bone 72 is penetrated, the elastic element 5 returns and pushes the bearings 2 away, moving the transmission shaft 3 away from the cutting rod 4. Thus, the transmission member 32 disengages from the coupling member 43. As a result, the transmission shaft 3 cannot drive the cutting rod 4 to rotate, the cutting rod 4 stops rotating, and the cutter 41 stops cutting. This avoids the nasal membrane 73 of the patient from being lifted and injured.

Furthermore, at the moment the last cortical bone is penetrated, the transmission shaft 3 that has not yet completely stopped only rotates the inner races 22 of the two bearings 2 and the limiting ring 5. The cutting rod 4 that has stopped rotating also stops rotation of the sleeve 1 and the outer races 21 of the two bearings 2. The elastic element 5 abutting between the positioning member 42 of the cutting rod 4 and the outer races 21 of the bearings 2 also stops rotating. Thus, the elastic element 5 will not rotate relative to the positioning member 42 or the outer races 21 of the bearings 2, preventing a temperature rise of the cutting rod 4 resulting from frictional heat and avoiding wear of the elastic element 5, the positioning member 42, or the bearings 2.

Note that in a case that the bearings 2 are oily bearings, the rod 31 of the transmission shaft 3 extends through the bearings 2 and can rotate relative to the bearings 2 to achieve the same effect, which can be appreciated by one having ordinary skill in the art.

In view of the foregoing, the rotational smoothness of the transmission shaft 3 and the cutting rod 4 of the bone implant drill according to the present invention can be increased by the provision of the bearings 2. Of more importance, due to provision of the bearings 2, the elastic element 5 will not cause wear to nor will not be worn by the components that are still rotating or that have stopped rotating, prolonging the service life of the components, avoiding annoying noise during operation, and preventing temperature increase of the components contacting the object being drilled. Thus, when the bone implant drill is used to drill a bone of a creature (such as in a sinus lifting operation), the risks of osteonecrosis can be reduced, which is helpful to integration after the bone graft and grow maintenance, shortening the restoration time after the surgery.

Furthermore, during operation of the bone implant drill according to the present invention, the components will not have high heat resulting from friction therebetween, such that the elastic element 5 can maintain good elasticity to disengage the transmission member 32 from the coupling member 43 in an appropriate timing, reliably achieving the effect of the safety mechanism of the bone implant drill while permitting continuous operation to increase the drilling efficiency.

Furthermore, in the bone implant drill according to the present invention, the first and second ends of the elastic element 5 are supported from the inside and are, thus, less likely to twist and deform, which also assists in achieving the effect of the safety mechanism of the bone implant drill.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A bone implant drill comprising:
    a sleeve;
    a bearing received in the sleeve;
    a transmission shaft including a rod and a transmission member, with the rod extending through the bearing, with the transmission member formed on an end of the rod and received in the sleeve, with the transmission member including a free end with a plurality of first teeth, and with another end of the rod extending beyond the sleeve;
    a cutting rod including a cutter, a positioning member, and a coupling member, with the cutter and the coupling member provided on two ends of the cutting rod respectively, with the positioning member located between the cutter and the coupling member, with the coupling member received in the sleeve, and with the coupling member including a plurality of second teeth releasably engageable with the plurality of first teeth; and
    an elastic element mounted in the sleeve, with the elastic element including a first end mounted around the coupling member and abutting the positioning member, and with the elastic element further including a second end mounted around the transmission member and abutting the bearing.

2. The bone implant drill as claimed in claim 1, with the bearing including an inner race and an outer race surrounding the inner race, with the outer race and the inner race rotatable relative to each other, with the rod extending through and coupled to the inner race, with the rod and the inner race jointly rotatable, and with the second end of the elastic element abutting the outer race.

3. The bone implant drill as claimed in claim 2, with the transmission member having a diameter larger than a diameter of the rod, forming a shoulder at an interconnection between the transmission member and the rod, and with the shoulder abutting the inner race of the bearing and not abutting the outer race of the bearing.

4. The bone implant drill as claimed in claim 3, further comprising a limiting ring, with the rod of the transmission shaft extending through and coupled to the limiting ring, with the rod and the limiting ring jointly rotatable, with the bearing restricted between the limiting ring and the transmission member, and with the limiting ring abutting the inner race of the bearing and not abutting the outer race of the bearing.

5. The bone implant drill as claimed in claim 2, with the sleeve including a first end, with the first end of the sleeve being open, with the rod extending through the first end of the sleeve, with the sleeve further including an inner flange in the first end thereof, with the outer race of the bearing abutting the inner flange, and with the inner race of the bearing not abutting the inner flange.

6. The bone implant drill as claimed in claim 5, with the sleeve further including a second end, with the second end of the sleeve being open, with the positioning member of the cutting rod connected to the coupling member, with the positioning member having a diameter larger than a diameter of the coupling member, forming a shoulder at an interconnection between the positioning member and the coupling member, with the cutting rod coupled to the second end of the sleeve by the positioning member, and with the first end of the elastic element abutting the shoulder.

7. The bone implant drill as claimed in claim 1, with the plurality of second teeth meshed with the plurality of first teeth by rectilinear contact.

8. The bone implant drill as claimed in claim 7, with the cutting rod and the rod coaxial to each other, with the plurality of first teeth surrounding and centered on an axis of the rod, with the plurality of second teeth surrounding and centered on an axis of the cutting rod, with each of the plurality of first and second teeth including decreasing widths from a root thereof towards a free end thereof and including an outer face and an inner face opposite to the outer face, and with the free end of each of the plurality of first and second teeth extending arcuately from the outer face to the inner face.

9. The bone implant drill as claimed in claim 8, with the each of the plurality of first and second teeth further including two lateral faces connected between the outer face and the inner face, and with each of the two lateral faces inclining from the outer face towards the inner face such that the inner face is smaller than the outer face.

10. The bone implant drill as claimed in claim 1, further comprising another bearing, with the bearing and the another bearing coaxial to each other, and with the transmission shaft extending through the bearing and the another bearing.

\* \* \* \* \*